United States Patent [19]

Harvey

[11] Patent Number: Plant 7,063

[45] Date of Patent: Dec. 5, 1989

[54] APPLE TREE "GINGER GOLD"

[75] Inventor: Clyde H. Harvey, Lovingston, Va.

[73] Assignee: Adams County Nursery, Inc., Aspers, Pa.

[21] Appl. No.: 280,749

[22] Filed: Dec. 7, 1988

[51] Int. Cl.[4] ..... A01H 5/00

[52] U.S. Cl. ..... Plt./34

[58] Field of Search ..... Plt./34

*Primary Examiner*—Robert E. Bagwill

*Attorney, Agent, or Firm*—Frank B. Robb

[57] ABSTRACT

A variety of apple tree originating as a chance seedling of unknown origin discovered in a replanted Winesap orchard near Lovingston, Va., the variety producing glossy yellow green apples with good keeping qualities, early in the season and in fact substantially earlier than other quality yellowish apples, the new variety also being distinguished because of the smooth glossy skin free from russetting which is common on yellow skinned cultivars.

1 Drawing Sheet

BACKGROUND OF THE DISCLOSURE

This invention relates to apple trees and particularly to an apple which is similar to a Winesap and in this particular case is a chance seedling of unknown origin discovered in a replanted Winesap orchard near Lovingston, Va.

I have been in the apple growing business for many years, am a grower, packer and shipper of various varieties of apple such as a result am constantly on the lookout for new varieties which I feel will be of commercial importance.

This particular variety presently to be described, is such an apple and is one of the glossy yellow green type which is of very good quality and as an early season apple is substantially earlier than other similar or related apples.

There are certain aspects of this particular apple which have made the same outstanding and in particular caused me to observe it in the first place and watch the growth over a number of years to determine that it was in fact a variety which I felt desirable to promote and commercialize, and as a result summarize the same in detail in the following.

DETAILED DESCRIPTION OF THE INVENTION

My new and distinct variety of apple tree was discovered by me as a chance seedling in a Winesap apple block in my orchard near Lovingston, Va.

The tree first came to my attention and thus I believe is a new variety which was discovered in making a routine inspection of a replanted orchard some years ago. The variety was different from the usual Winesap trees because of the fruit's glossy, smooth, yellow green skin color and it was particular free of russetting.

The tree and its fruit were observed by me for a number of years and compared to many varieties in my orchard and those packed and shipped by my company.

Relatively recently, in the summer, buds were collected and trees were propagated. I caused the same to be planted in my orchard, and in continued evaluation of these trees, the fruit, leaves and tree characteristics were found to be identical to the parent tree discovered by me as a chance seedling.

Trees of the new variety herein described have exhibited a medium strong, vigorous growth habit similar to other golden apple varieties having good hardiness, medium but regular annual productivity. They are large, somewhat variable in space, glossy, brilliant yellow green apples produced by the tree hereof.

The fruit is free from russetting which is common on many yellow green apples. The flesh is white with a greenish tint, tender, fine, juicy and of a firmness which is unusual for early maturing apples.

The apple itself is easily handled with little skin or flesh blemish and can be stored for substantial periods of time with little deterioration in quality.

My new variety matures from about July 25 to August 15, well ahead of most golden apple varieties.

As compared with other varieties which ripen in this season, the other varieties are not nearly as firm, are of mediocre quality and have very limited storage life.

I have caused the apple of my new variety to be asexually reproduced and have demonstrated that its combination of characteristics comes true and is established and transmitted through succeeding generations.

The specimens to be described and shown herein were grown and observed near Lovingston, Va.

I have chosen to call my new variety "Ginger Gold" since that seems to be a good commercial name by which the same may be identified and in the accompanying photograph which forms the drawing hereof.

There is shown typical specimens of the fruit and foliage of my new variety as depicted in color in a photograph as nearly true as is reasonably possible to make the same in a color illustration of this character and references to color where made, are to the Nickerson Color Fan published by Munsell Company and notations indicated thereon.

There follows a detailed description of my new variety with many of the aspects particularly pointed out.

Dates of first and last picking: July 25 and Aug. 15, 1988.

Tree: Medium, large, medium vigorous, spreading to slightly drooping, round topped, rapid growing, hardy, medium productive, and regularly productive.

*Trunk.*—Medium stocky and medium smooth.

*Branches.*—Medium thick to slender, medium smooth, moderate branching. Color — Brownish gray 10 YR3/1.

*Leaves.*—Length — approximately 3¼ inches. Width — approximately 2¼ inches. Large, medium wide, medium long, ovate, abruptly pointed, medium thick. Color — Strong yellow green 10GY $\frac{5}{8}$. Margin — Smooth to finely serrate. Petiole — Medium short and medium thick.

*Flowers.*—Date of first bloom — Apr. 15, 1988. Date of full bloom — May 1, 1988. Medium, medium large flower, white with pinkish center.

*Fruit.*—Maturity when eating ripe — Aug. 1, 1988. Size — Variable, axial diameter $2\frac{7}{8}$ inches. Transverse diameter — $2\frac{5}{8}$ inches. Oblate to conical, variable shape and truncate at base. Cavity — Symmetrical, obtuse at apex, russet to smooth green. Depth — approximately $\frac{3}{8}$ inch. Breadth — approximately 1 inch. Basin — Unsymmetrical, furrowed, undulate. Depth — Approximately $\frac{1}{4}$ inch. Breadth — $\frac{7}{8}$ inch. Stem — Slender, medium long, pubescent. Length — approximately 1 inch. Breadth — 1/16 inch. Calyx — Closed, segments — persistent, acuminate Length — Approximately 3/16 inch, reflexed from base at apex. Eye — Medium and open. Skin — Medium tender, medium thin, smooth, glossy, Dots wanting, many, small, even, arolar. Color of dots — Russet green. Dots evenly distributed. Ground color — Strong greenish yellow 10Y 8/11. Color markings — blushed and dull. Bloom — Moderate, general color effect — Brilliant yellow green 25 GY 9/8. Flesh —

Juicy, color — White with greenish tint. Texture — Firm, tender, fine, crisp. Flavor — Mild to tart, sprightly. Aroma — Wanting. Quality — Good. Core — Median. Bundle area — Large, orbicular, unsymmetrical at base. Unequal halves of area. Bundles — Greenish white, conspicuous, in two whorls. Core line — Meeting. Calyx tube — Glabrous toward base Depth of tube to shoulder $\frac{1}{2}$ inch. Entire depth $\frac{1}{2}$ inch. Auxillary cavity present. Seed cells open. Seeds — Number perfect — 8. Number imperfect — 0. Number in one cell — 2. Length — $\frac{3}{8}$ inch. Breadth — $\frac{1}{4}$ inch. Form — Acute. Color — Strong yellowish brown 10 YR 5/6.

*Use.*—Dessert. Keeping quality — Very good. Average tolerance to insects and diseases.

I claim:

1. A new and distinct variety of apple tree originating as a chance seedling in a Winesap apple block, substantially as herein shown and described characterized particularly as to novelty by the early season of its maturity, the smooth, glossy, brilliant yellow green skin color on the fruit, very long storage life of said fruit, and the unique combination of characteristics which are very different from other yellow green apple cultivars.

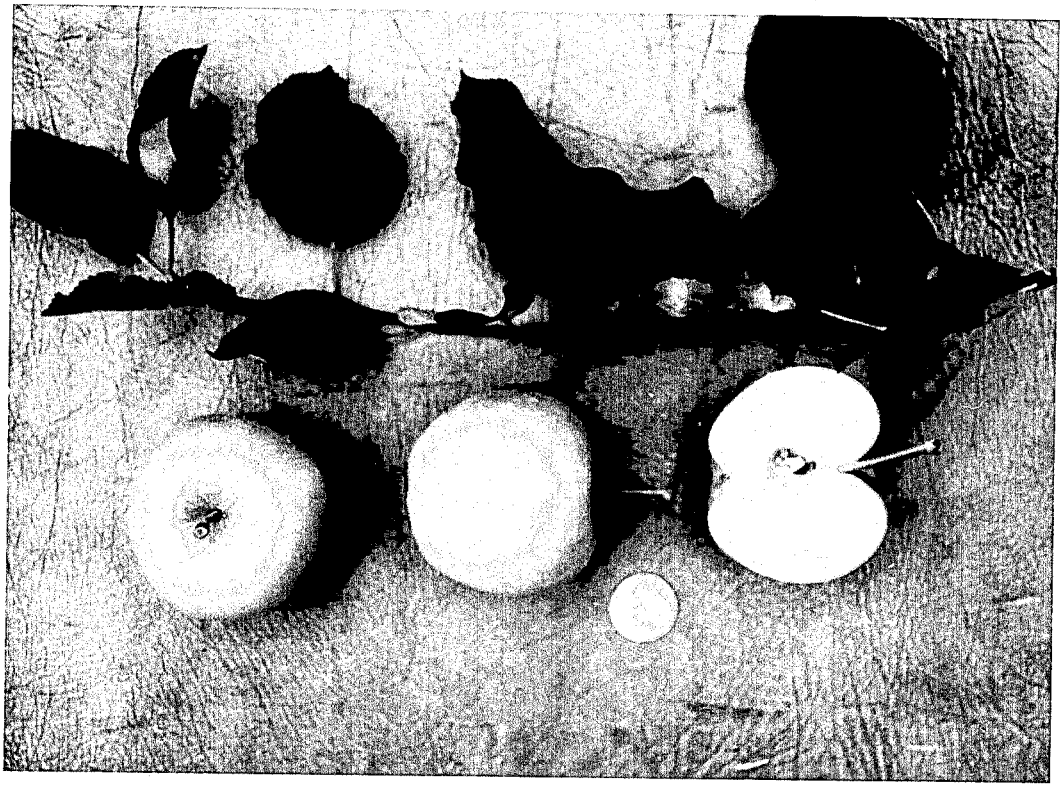

* * * * *